United States Patent
East

[11] Patent Number: 5,963,453
[45] Date of Patent: Oct. 5, 1999

[54] SYSTEM AND METHOD FOR PROCESSING PRESCRIPTION MEDICATIONS

[75] Inventor: Elvin E. East, Cordele, Ga.

[73] Assignee: Medication Management, Inc., Cordele, Ga.

[21] Appl. No.: 08/976,736

[22] Filed: Nov. 24, 1997

Related U.S. Application Data

[60] Provisional application No. 60/031,744, Nov. 25, 1996.

[51] Int. Cl.⁶ .................................................... G06F 7/00
[52] U.S. Cl. ................. 364/479.14; 364/479.12; 364/479.01; 53/493
[58] Field of Search ............... 364/479.14, 479.05, 364/479.12, 479.01; 53/493; 221/9, 10

[56] References Cited

U.S. PATENT DOCUMENTS

| | | | |
|---|---|---|---|
| 3,712,507 | 1/1973 | Holt | 221/82 |
| 3,754,374 | 8/1973 | Haines | 53/373 |
| 3,998,356 | 12/1976 | Christensen | 221/2 |
| 4,572,403 | 2/1986 | Benaroya | 221/3 |
| 4,604,847 | 8/1986 | Moulding et al. | 53/75 |
| 4,655,026 | 4/1987 | Wigoda | 53/55 |
| 4,674,651 | 6/1987 | Scidmore et al. | 221/3 |
| 4,690,676 | 9/1987 | Moulding et al. | 604/189 |
| 4,695,954 | 9/1987 | Rose et al. | 364/413 |
| 4,733,362 | 3/1988 | Haraguchi | 364/479 |
| 4,781,696 | 11/1988 | Moulding et al. | 604/189 |
| 4,785,969 | 11/1988 | McLaughlin | 221/2 |
| 4,809,877 | 3/1989 | Albright | 221/75 |
| 4,811,764 | 3/1989 | McLaughlin | 141/98 |
| 4,847,764 | 7/1989 | Halvorson | 364/413.02 |
| 4,918,604 | 4/1990 | Baum | 364/413.01 |
| 4,953,745 | 9/1990 | Rowlett, Jr. | 221/5 |
| 4,972,657 | 11/1990 | McKee | 53/411 |
| 5,044,516 | 9/1991 | Hoar | 221/2 |
| 5,097,652 | 3/1992 | Inamura et al. | 53/493 |
| 5,097,982 | 3/1992 | Kedem et al. | 221/3 |
| 5,152,422 | 10/1992 | Springer | 221/2 |
| 5,159,581 | 10/1992 | Agans | 386/10 |
| 5,176,285 | 1/1993 | Shaw | 221/3 |
| 5,208,762 | 5/1993 | Charhut et al. | 364/478 |
| 5,239,491 | 8/1993 | Mucciacciaro | 364/569 |
| 5,246,136 | 9/1993 | Loidl | 221/3 |
| 5,348,061 | 9/1994 | Riley et al. | 141/104 |
| 5,468,110 | 11/1995 | McDonald et al. | 414/273 |
| 5,490,610 | 2/1996 | Pearson | 221/2 |
| 5,502,944 | 4/1996 | Kraft et al. | 53/55 |
| 5,564,593 | 10/1996 | East | 221/3 |

Primary Examiner—William E. Terrell
Assistant Examiner—Khai H. Tran
Attorney, Agent, or Firm—Thomas, Kayden, Horstemeyer & Risley, L.L.P.

[57] ABSTRACT

A system and method for batch processing or filling prescriptions. Broadly stated, the prescription processing system comprises a packaging subsystem, a sorting subsystem, an optional medical reclamation subsystem, a system controller and prescription input means. The packaging subsystem, sorting subsystem and medical reclamation subsystem are all under the direction of the system controller. The system controller is in communication with prescription input device means, which is typically a plurality of remote terminals located at pharmacies, drug stores and hospitals. The prescription input device transmits prescription orders to the system controller where they are analyzed and sorted according to predetermined criteria to formulate a batch. The prescriptions are then packaged and sorted under the supervision of the system controller.

10 Claims, 18 Drawing Sheets

SYSTEM AND METHOD FOR PROCESSING PRESCRIPTION MEDICATIONS

CROSS REFERENCE TO RELATED APPLICATION

This application claims the benefit of U.S. Provisional Application Ser. No. 601031,744, filed Nov. 25, 1996. The above referenced provisional application is incorporated herein by reference.

BACKGROUND OF THE INVENTION

1. Field of the Invention

The present invention relates generally to the field of packaging medication, and more particularly to an automated system and method for processing prescriptions.

2. Description of Related Art

According to statistics published by the National Association of Retail Drug Stores (NARD) Lily Digest in 1994, small to medium sized pharmacies averaged only four prescriptions per hour. Because of the low productivity rate for packaging and labeling prescriptions, a very high variable cost is incurred in filling each prescription. Larger stores had higher productivity rates, but these rates were achieved at the cost of adding more pharmacists and assistants to shelve and replace medications, count medications, and label the prescriptions. Large hospitals and mail order pharmacies use automated machinery to package and label prescriptions; however, the equipment they use is far too expensive for the average pharmacy to own and operate.

Computers and bar code technology have long been used to control the packaging of medications and pharmaceuticals in a manufacturing or wholesale environment. Furthermore, computers and bar code technology are used extensively in the health care field to maintain medication inventories, order medications, maintain patient medication profiles and create labels for prescriptions.

Nevertheless, computers and bar code technology are not used at the retail level because the random nature of filling prescriptions makes computer controlled automation of the process impractical. However, a close examination of the pattern of these prescriptions reveals that most prescription medications are refilled on a monthly or regular basis.

What is therefore sought after is a system that uses the historical patterns of incoming prescription orders to batch prescription orders together such that traditional automation techniques can be economically applied to processing or filling the prescriptions.

Just as computer controlled automation has yet to penetrate the retail medication industry, recycling concepts, so prevalent in the rest of society, have similarly not been applied to prescription medications. For example, in a nursing home, it is customary to deliver a 30 day supply of prescription medication for each patient's use. If the patient dies or the prescription is discontinued by the patient's doctor, any unused portion of the prescription is required to be destroyed under U. S. Food and Drug Administration (FDA) and state pharmacy regulations. This practice is mandated because no technology is currently available for safely reclaiming and recycling these medications. With health care costs spiraling ever higher, elimination of wasteful practices, such as destroying useful drugs and medicine, becomes ever more important.

What is needed, therefore, is a system and process that is both safe and effective at reclaiming and recycling these heretofore wasted medications.

SUMMARY OF THE INVENTION

Certain objects, advantages and novel features of the invention will be set forth in the description that follows and will become apparent to those skilled in the art upon examination of the following or may be learned with the practice of the invention. The objects and advantages of the invention may be realized and obtained by means of the instrumentalities and combinations particularly pointed out in the appended claims.

To achieve the advantages and novel features, the present invention is generally directed to a system and method for batch processing or filling prescriptions. Broadly stated, the prescription processing system comprises a packaging subsystem, a sorting subsystem, an optional medical reclamation subsystem, a system controller and prescription input means. The packaging subsystem, sorting subsystem and medical reclamation subsystem are all under the direction of the system controller. The system controller is in communication with prescription input means, which is typically a plurality of remote terminals located at pharmacies, drug stores and hospitals. The prescription input means transmits prescription orders to the system controller where they are analyzed and sorted according to predetermined criteria to formulate a batch. The prescriptions are then packaged and sorted under the supervision of the system controller.

According to the invention, the packaging subsystem includes a conveyor that transports medication containers between labeling/packaging apparatus, container identification apparatus and medication dispensing apparatus. To guarantee the integrity of the packaging subsystem, the container identification apparatus transmits medication and patient profile information back to the system controller where consistency checks are made. The medication dispensing apparatus comprises an electronic medication counter and a uniquely designed filling apparatus for loading the medication into the container.

According to another aspect of the present invention, the sorting subsystem comprises distribution and sorting conveyors. Identification apparatus is used to transmit sort criteria information from the medication containers on the distribution conveyor back to the system controller, which activates redirection apparatus to separate the matched container from the other containers.

A medication reclamation subsystem can be used to recover unused medication from packaged medication containers. The medication reclamation subsystem includes a conveyor that transports packaged medication containers between identification apparatus and extraction apparatus. Again, for integrity purposes, the identification apparatus transmits medication identification information back to the system controller where a verification check is made to ensure that medication is not mixed during the extraction process. The extraction apparatus comprises an extraction disc having a plurality of customized posts extending therefrom for penetrating the medication container and dislodging the medication.

Additional advantages will become apparent from a consideration of the following description and drawings:

BRIEF DESCRIPTION OF THE DRAWINGS

Other features of the present invention will be more readily understood from the following detailed description of specific embodiments thereof when read in conjunction with the accompanying drawings, in which.

DESCRIPTION OF THE PREFERRED EMBODIMENT

Figure 1:
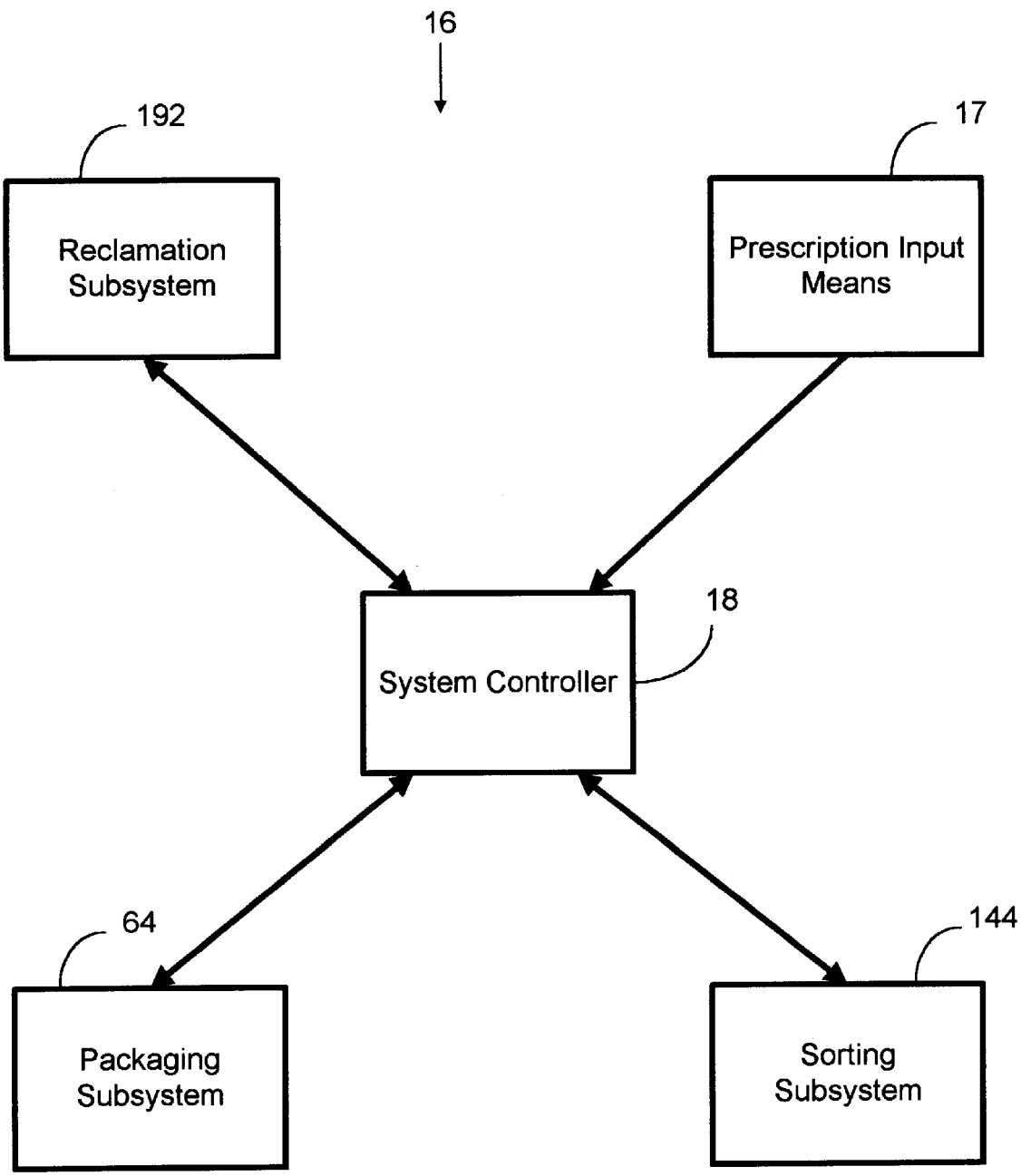
FIG. 1 is a block diagram of a prescription processing system according to the instant invention.

While the invention is susceptible to various modifications and alternative forms, a specific embodiment thereof is shown by way of example in the drawings and will herein be described in detail. It should be understood, however, that there is no intent to limit the invention to the particular form disclosed, but on the contrary, the invention is to cover all modifications, equivalents, and alternatives falling within the spirit and scope of the invention as defined by the claims.

A high level, architectural view of a prescription processing system 16 according to the instant invention is shown in FIG. 1. Prescription processing system 16 includes a system controller 18 that receives prescription orders from prescription input means 17. System controller 18 analyzes and sorts these prescriptions into a batch or batches that are then processed or filled through packaging subsystem 64 and sorting subsystem 144. Moreover, the prescription processing system includes an optional reclamation subsystem 192 for recovering unused medication from prescription containers.

Figure 2:
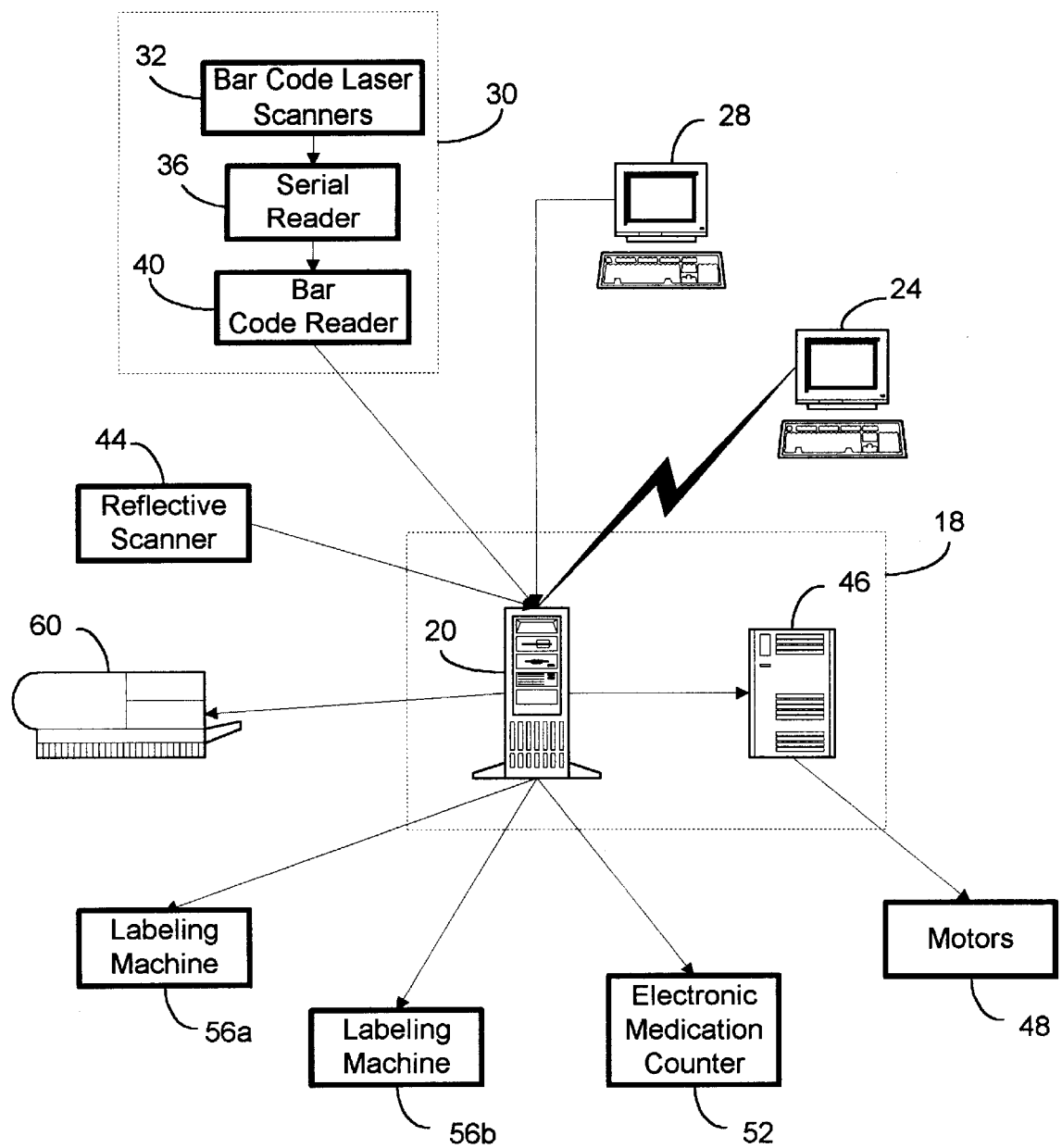
FIG. 2 is a block diagram of the system controller and the prescription processing system's various input and output components.
Figure 3:
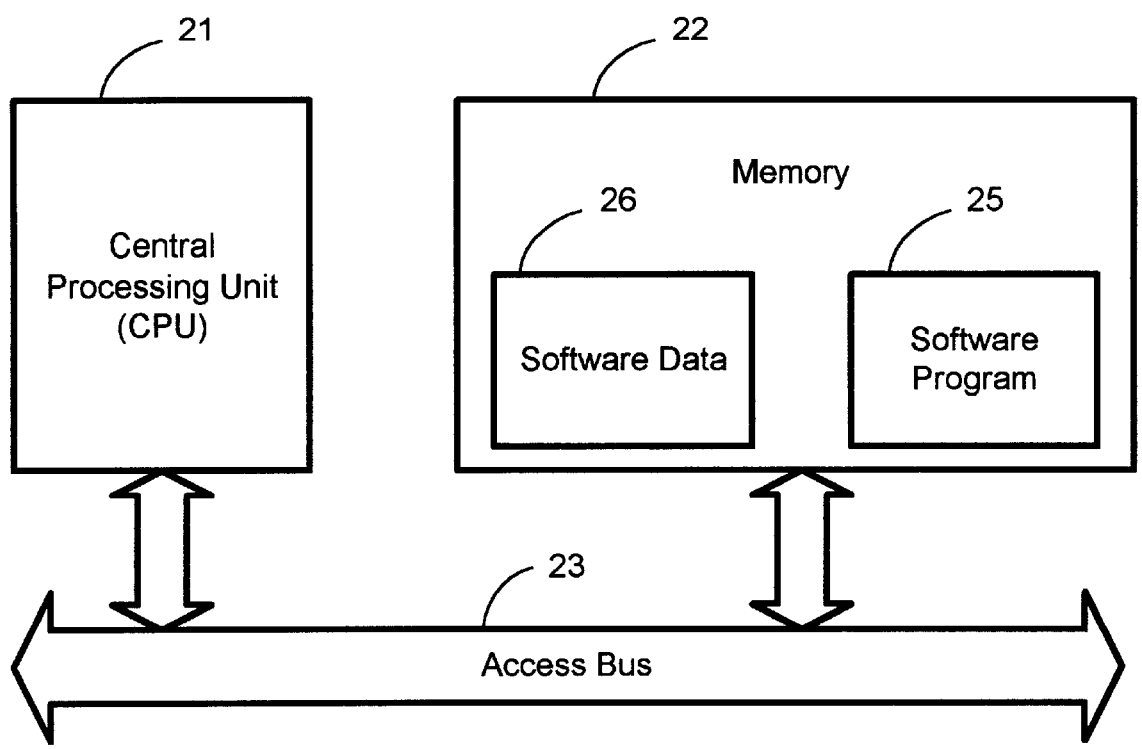
FIG. 3 is a block diagram of a computer for use in the prescription processing system.

FIG. 2 illustrates the relationship between the various input and output devices in communication with system controller 18. System controller 18 is comprised of computer 20 and programmable logic controller (PLC) 46. Computer 20, which can be a standard microcomputer or workstation, is configured with a plurality of communication ports for receiving and transmitting control signals and information. Alternatively, computer 20 can be accompanied by a communication server to facilitate communication among the several system components. Turning now to FIG. 3, a basic architecture for computer 20 is shown. Computer 20 includes a central processing unit (CPU) 21 and memory 22, which is a logical representation of the various memory media present in a standard computer (e.g., CD ROM, floppy disk, hard disk, RAM, ROM, cache, etc.). CPU 21 accesses memory 22 over access bus 23 to run software program 25 and manipulate software data 26. Software program 25 and software data 26 provide the "intelligence" (i.e., logic capability) for processing system 16.

Returning back to FIG. 2, computer 20 receives input from prescription input means 17, which is comprised of pharmacy terminals 24 and control terminal 28. Pharmacists and medical personnel transmit prescription orders from pharmacy terminals 24 generally through direct dialed connections over the public switched telephone network (PSTN). Pharmacy terminals 24 are typically remotely located at the various pharmacies, drug stores and hospitals that subscribe to the prescription processing service provided by the instant invention. It is envisioned that access to the prescription processing service will also be provided over the Internet via interaction with a page on the World Wide Web (WWW). A second device used for input to computer 20 is control terminal 28. Control terminal 28 may be a microcomputer or a dumb terminal and can be directly connected to computer 20 via an RS232 communication port or a local area network (LAN).

Prescriptions that are phoned in or sent in by facsimile can be entered through control terminal 28 by a local operator. Moreover, control terminal 28 will also be used for performing maintenance on prescription processing system 16 and for interacting with and updating software program 25 on computer 20. A third source of input to computer 20 is identification means 30, which is used in packaging subsystem 64, sorting subsystem 14 and reclamation subsystem 192 and comprises a plurality of bar code laser scanners 32 daisy chained through serial reader 36. Serial reader 36 is connected to bar code reader 40, which contains an output port for transmitting bar code information to computer 20 via an RS232 communication port. Lastly, a reflective scanner 44 is also connected to computer 20 via an RS232 communication port.

System controller 18 is comprised of computer 20 in conjunction with PLC 46 and provides the system processing functionality and generation of control signals for the prescription processing system's output devices. These output devices include a plurality of motors 48 used throughout prescription processing system 16 that are controlled by computer 20 through PLC 46. An electronic medication counter 52 and two labeling machines 56a and 56b are connected to computer 20 via RS232 communication ports and are used in packaging subsystem 64. Finally, a printer 60 is optionally connected to computer 20 either directly or indirectly via a LAN for printing items such as transmissions from pharmacies, batch production control reports, inventory control reports, shipping reports and general purpose printing.

With frequent reference to the figures, the architecture and operation of the subsystems (i.e., packaging subsystem 64, sorting subsystem 144 and reclamation subsystem 192) of prescription processing system 16 will be discussed hereinafter.

Packaging Subsystem

Figure 4A:
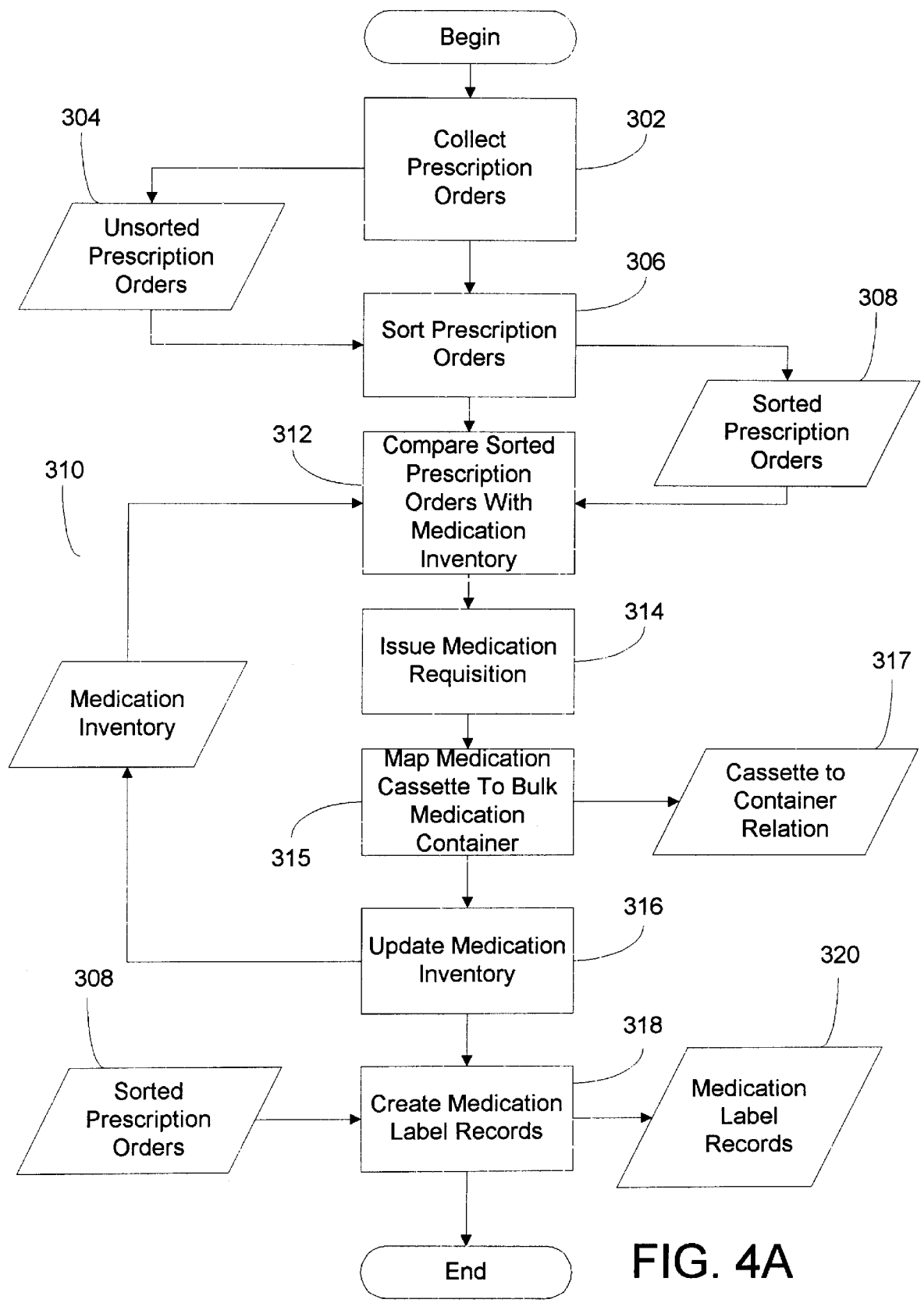
FIGS. 4A, 4B and 4C are flow charts representing programming tasks and data associated with prescription packaging.
Figure 4B:
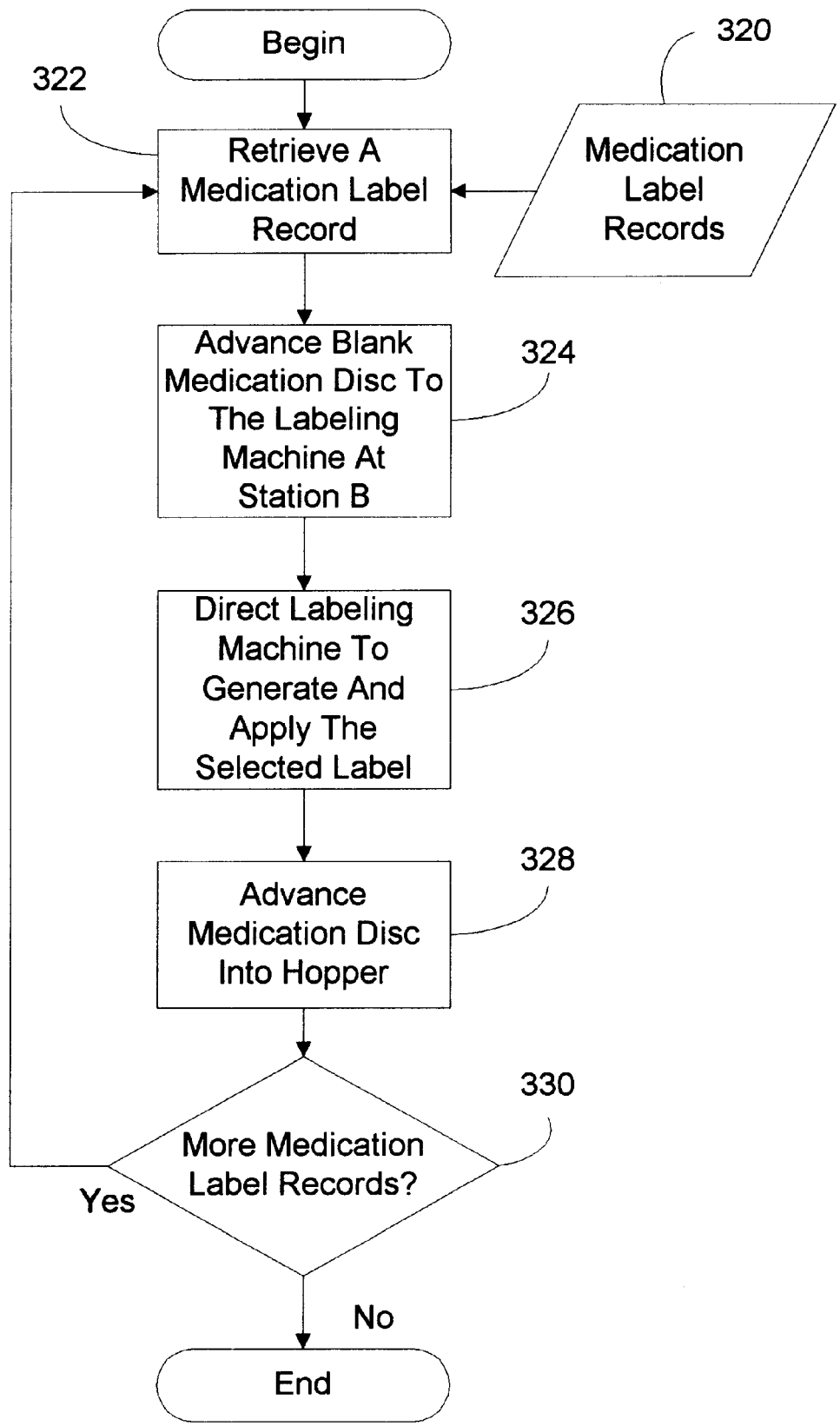
Figure 4C:
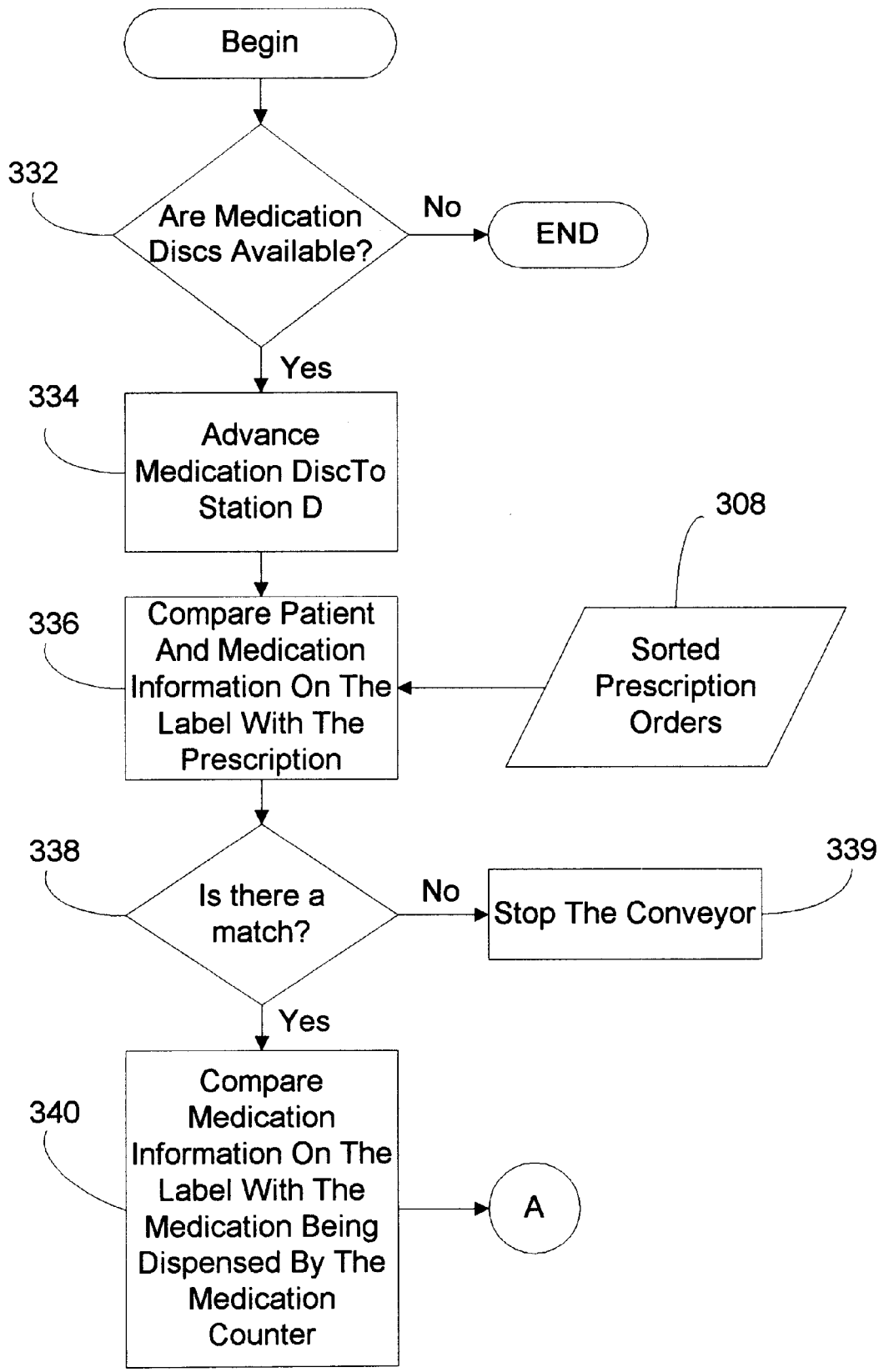
Figure 4D:
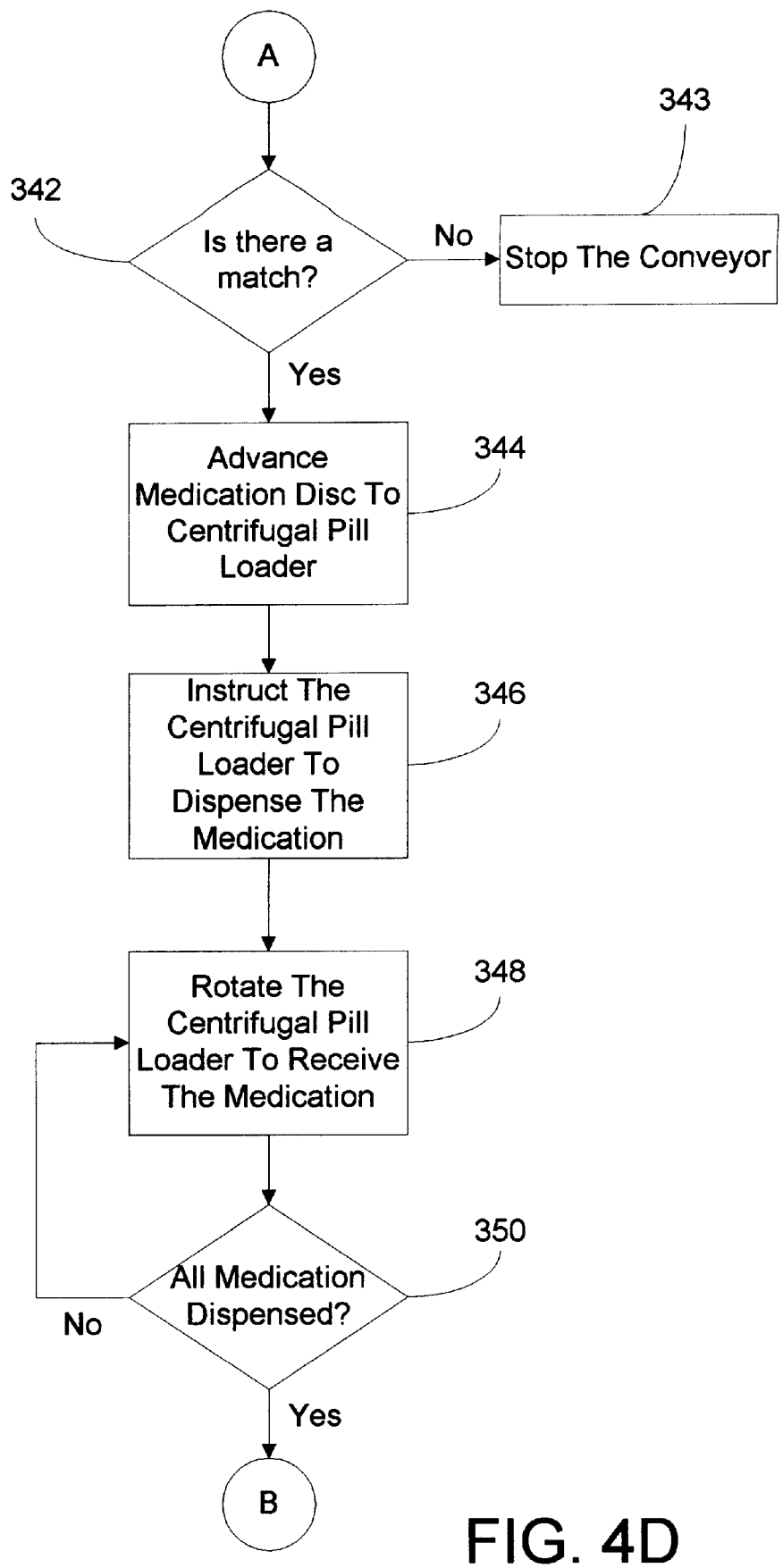
Figure 4E:
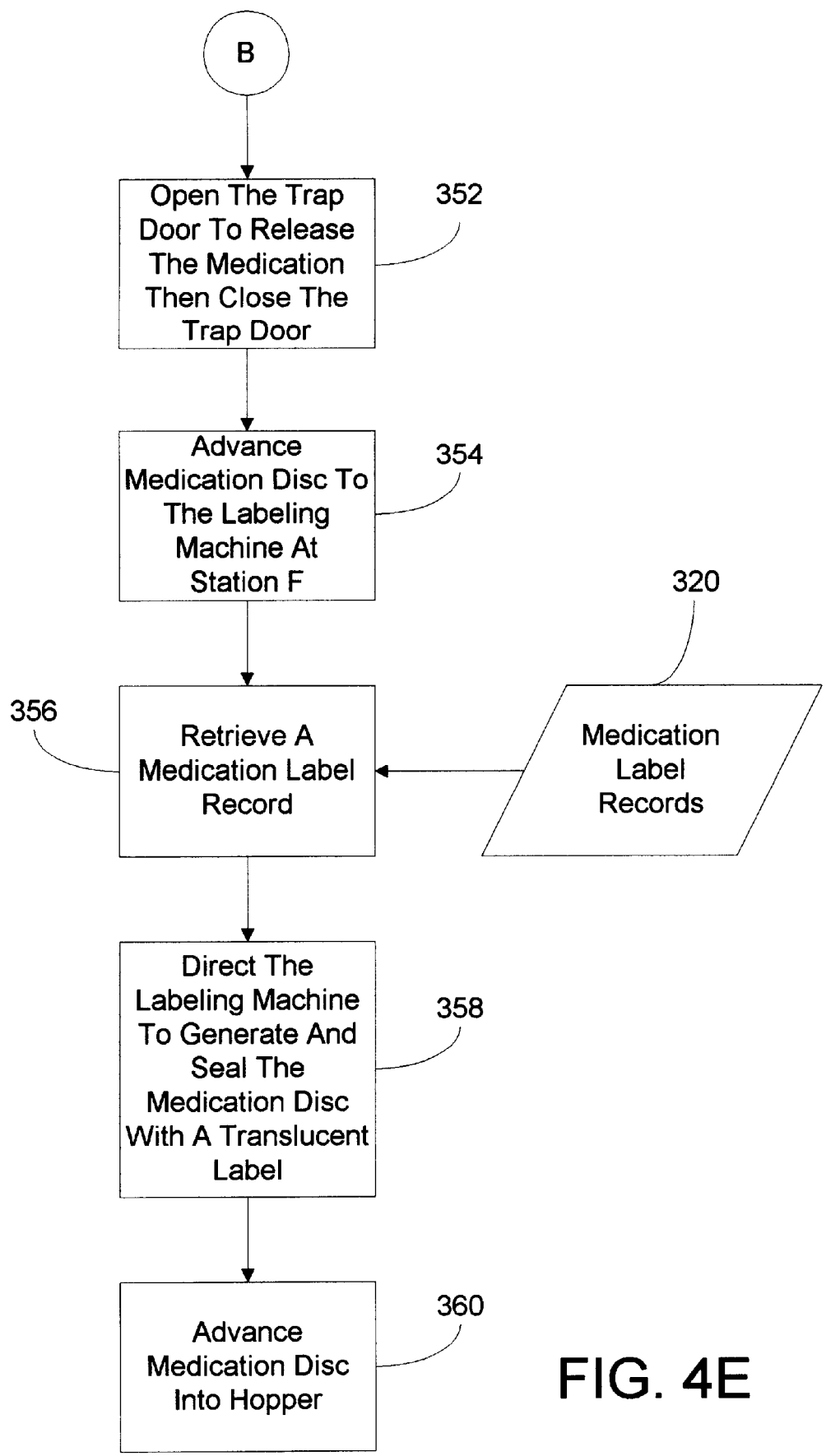

FIGS. 4A, 4B, and 4C are flow charts representing programming tasks and data associated with packaging subsystem 64. These figures will be the subject of frequent reference throughout the discussion of packaging subsystem 64.

FIG. 4A depicts the sequence of steps that occur before prescription packaging begins. First, computer 20 collects prescription orders transmitted from pharmacy terminals 24 in step 302 and stores them in a data structure 304. Once a sufficient number of orders have been submitted, the orders will then be sorted into batches by software program 25 in step 306 and stored in a data structure 308. The orders are typically sorted according to retail pharmacy number, patient number, medication manufacturer's code and medication quantity. Moreover, orders may be placed into batches according to expected incoming order requests based on historical patterns. The size of the batches can be chosen by the operator based on prescription request patterns and optimum medication quantities for the various packaging apparatus. By analyzing the incoming orders and arranging them into batches for processing or filling, the instant invention creates an economy of scale whereby application of automated systems becomes practical. At this point, the orders in sorted prescription data structure 308 and the inventory of medications in data structure 310 are compared in step 312. A requisition will then be prepared in step 314 and printed on printer 60 that authorizes removal of a sufficient quantity of each ordered medication from storage and transferal of that medication into production cassettes for processing. As part of this transfer, checks are made to ensure that the medications have not passed their expiration dates and that they will not expire before the intended administration date. Preferably, the bulk medication containers in storage are bar coded such that they can be tied to the production cassettes thereby allowing potential errors to be traced all the way back to the medication supply. This can be accomplished by scanning both the bulk medication container and a bulk production cassette with a laser scanner 32 and storing this relationship in a data structure 317 in step 315 after processing by software program 25. Medication inventory data structure 310 is then updated in step 316 to reflect the removal of the ordered medications. Finally, medication label records are generated in step 318 and stored in data structure 320 based on the sorted prescription orders in data structure 308.

Figure 5:
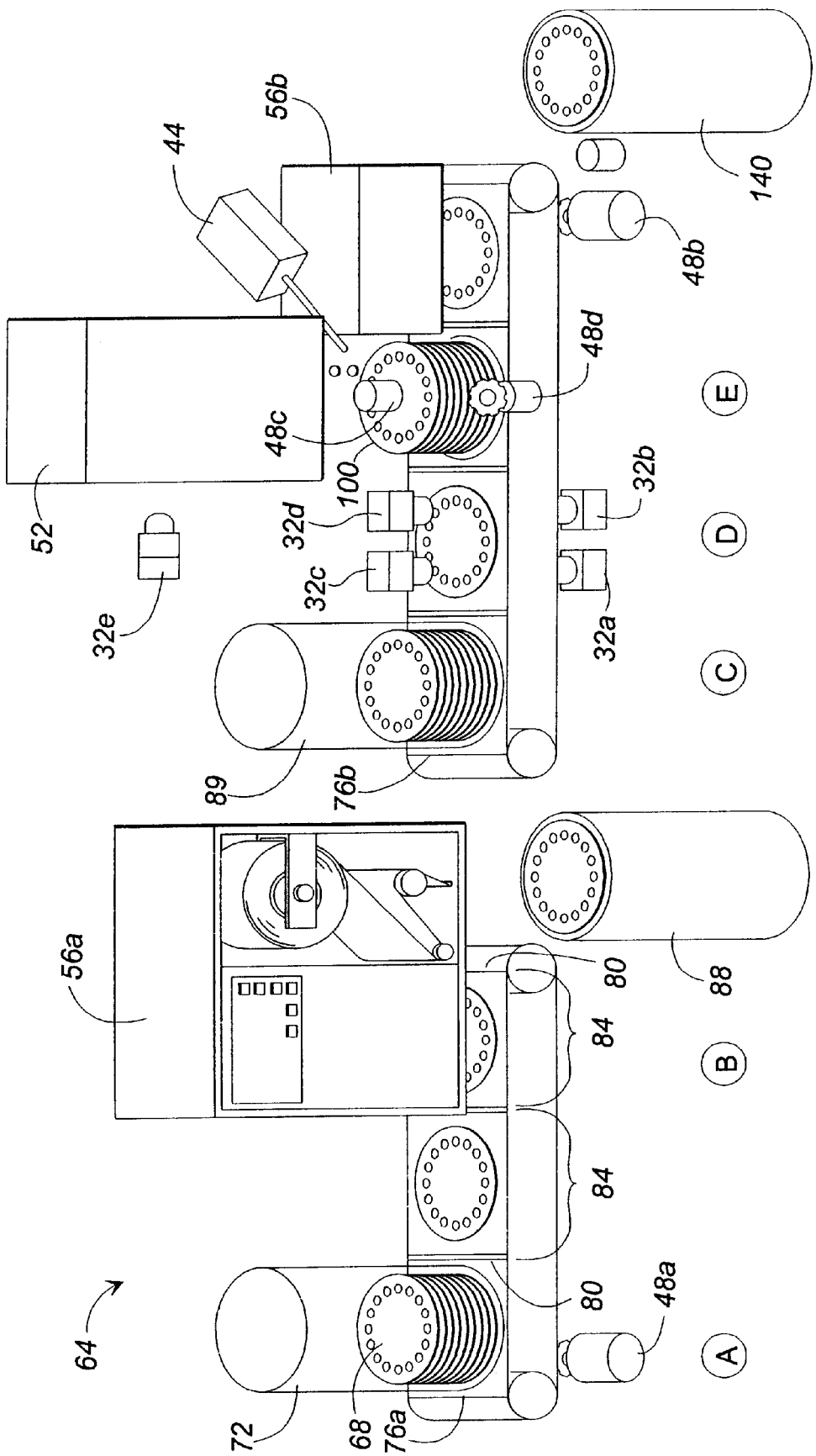
FIG. 5 is a perspective view of the packaging subsystem according to the instant invention.

With the bulk quantities of prescription medications now amassed for production, the packaging and labeling of individual medication containers can begin. FIG. 5 illustrates a preferred architecture of prescription packaging subsystem 64 according to the instant invention. The architecture and relationship of the individual components illustrated in FIG. 5 will be described in conjunction with the packaging process set forth in the flow charts of FIGS. 4B and 4C.

As shown in FIG. 5, blank medication discs 68 are manually loaded into hopper 72, which holds approximately one-thousand discs and is suspended above conveyor belt 76a by a distance approximating the width of one medication disc. Because of their commonality, medication discs 68 are illustrated as an exemplary container; however, alternative types of medication containers could also be used with minimal modification to the components of the present invention. Conveyor belts 76a,b are uniquely designed to receive medication discs from hopper 72. Specifically, conveyor belts 76a,b are constructed from a molded flexible plastic material approximately ⅛" thick with 1/16" depressions formed therein that are shaped to the contours of a medication disc. Furthermore, conveyor belts 76a,b include markers 80 that define sections 84 in the belts that encompass a single medication disc 68. With reference now to both FIG. 5 and FIG. 4B, software program 25 in step 322 retrieves a medication label record from data structure 320. Software program 25 will then, in step 324, trigger a signal from computer 20 to PLC 46 that instructs motor 48a to advance conveyor belt 76a by a distance approximately equal to a single section 84, which supplies an empty depression at station A for receiving a blank medication disc 68 from hopper 72. This procedure will continue until a blank medication disc 68 reaches station B. A blank medication disc 68 is gravity fed from hopper 72 each time an empty depression is cycled into position.

Once a medication disc 68 reaches station B, software program 25 in step 326 will transmit information from computer 20 to labeling machine 56a for preparation and application of a label to the blank medication disc 68. The information included on this label includes the patient's bar code number, the pharmacist's bar code number, the medication bar code number, the medication expiration date bar code number, administration instructions and the doctor's bar code number. After this label is applied, the blank medication disc 68 is then advanced off the end of conveyor and into hopper 88 in step 328. The process of labeling blank medication discs 68 will continue until all of the medication label records 320 are exhausted as indicated by decision diamond 330.

When hopper 88 is substantially filled with empty, labeled medication discs 68, hopper 88 is manually inverted and positioned above conveyor belt 76b as hopper 89 at station C. It will be appreciated that an automated or robotic system could also be used to invert hopper 88 and relocate the hopper to station C. Hopper 89 supplies the discs to conveyor belt 76b in the same manner as discussed hereinbefore with respect to hopper 72 and conveyor belt 76a. Similar to the control of conveyor belt 76a, the movement of conveyor belt 76b is controlled by software program 25 through PLC 46 and motor 48b.

Figure 6:
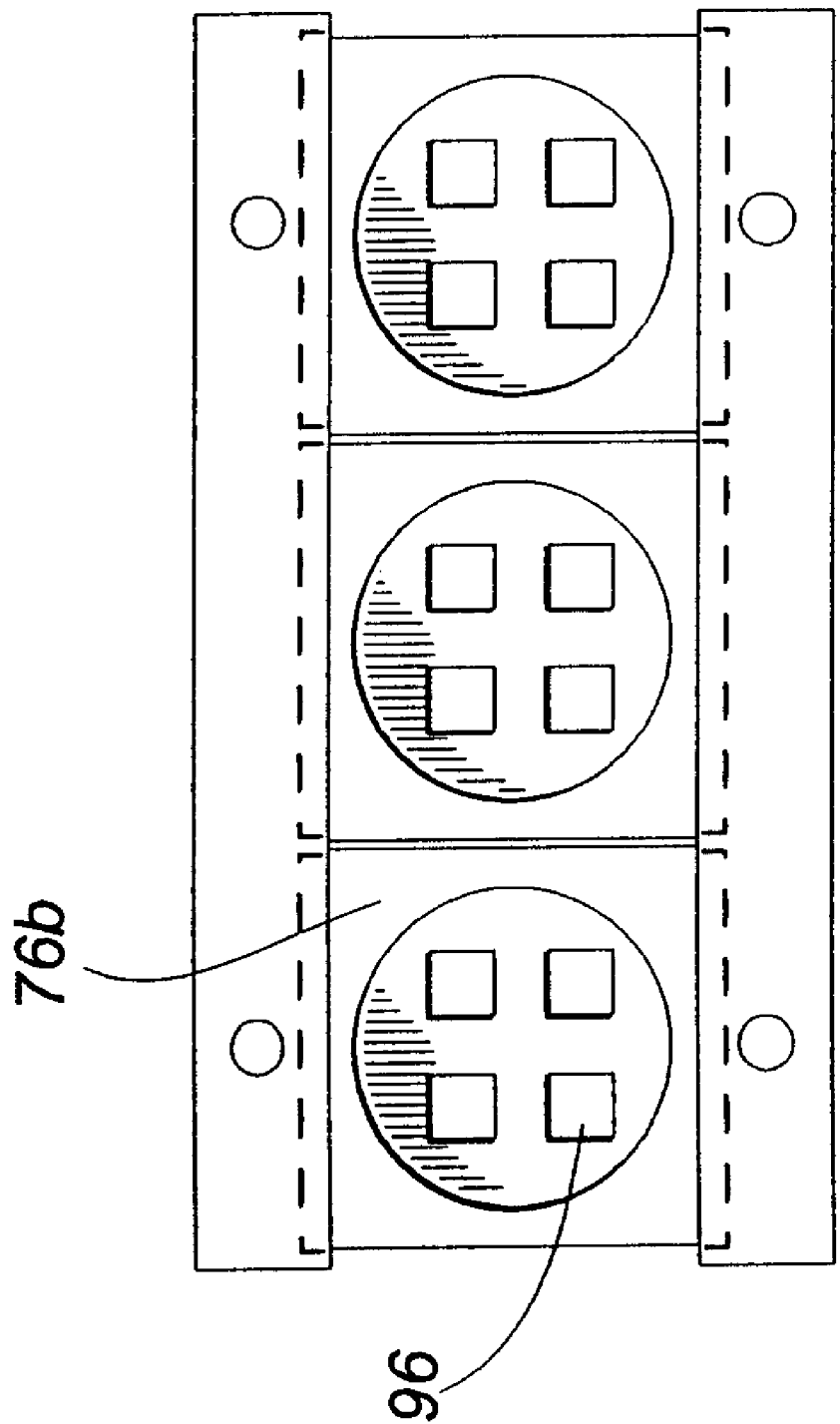
FIG. 6 is a plan view of the conveyor belt used in the packaging and sorting subsystems.

Referring now to FIGS. 4C and 5, the process continues at decision diamond 332 when medication discs 68 are made available to conveyor belt 76b. After being deposited onto conveyor belt 76b from hopper 89 at station C, Software program 25 in step 334 will then cause a labeled medication disc 68 to be advanced from station C to station D where several bar code scanners 32a,b,c,d are positioned below medication disc 68 to read the bar codes on the label. As shown in FIG. 6, conveyor belt 76b includes four bar code read windows 96 in each depression area where medication discs are held. These read windows 96 align with bar codes on the label of a medication disc 68 and also align with a set of other read windows 96 in a currently unfilled depression on the underside of conveyor belt 76b. Bar code scanners 32a,b,c,d then transmit bar code information such as patient number, pharmacist number and medication number to serial reader 36 where the information is then delivered to computer 20 via bar code reader 40. The label information is then compared in step 336 with the patient and medication information contained in the prescription orders stored in data structure 308. If the information is not consistent, then software program 25 will initiate a signal from computer 20 to shut down conveyor belt 76b via PLC 46 and motor 48b as indicated by decision diamond 338 and step 339. Another bar code scanner 32e is mounted adjacent the bulk medication cassette (not shown) holding the medications in electronic medication counter 52 and, likewise, transmits the medication identification number to computer 20 via serial reader 36 and bar code reader 40. Software program 25 compares the data from the medication disc 68 label with the medication identification data from the electronic medication counter 52 in step 340 to ensure that the prescription is being filled properly. Again, if the information is inconsistent, software program 25 initiates a signal from computer 20 to shut down conveyor belt 76b via PLC 46 and motor 48b as indicated by decision diamond 342 and step 343. Concerns about the medication contained in the bulk medication cassette can be resolved by software program 25 reading data structure 317 (see FIG. 4A) to determine the bulk medication container from which the medication cassette was filled. Once the error or errors are corrected, the labeled and now verified medication disc 68 is advanced to station E in step 344.

Figure 7B:
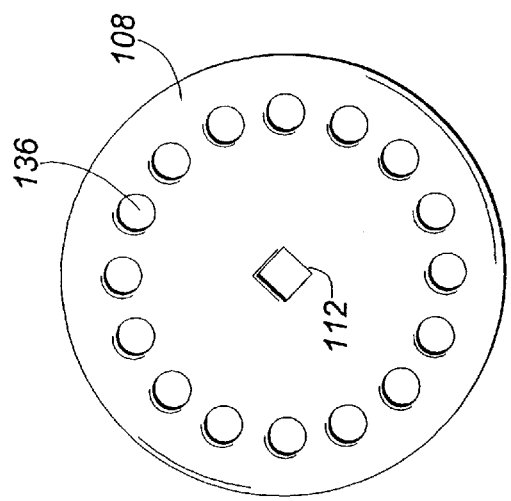
FIG. 7B is a plan view of a medication disc template that is used with the centrifugal pill loader.
Figure 7C:
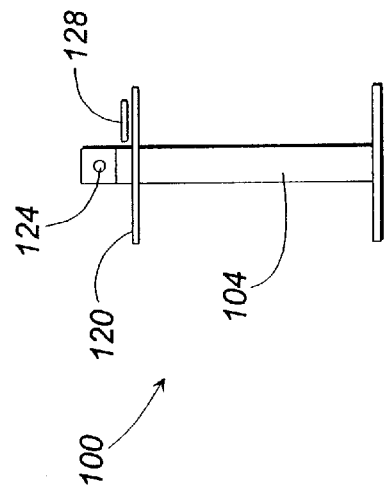
FIG. 7C is an elevation view of the centrifugal pill loader without any medication disc templates installed.
Figure 7A:
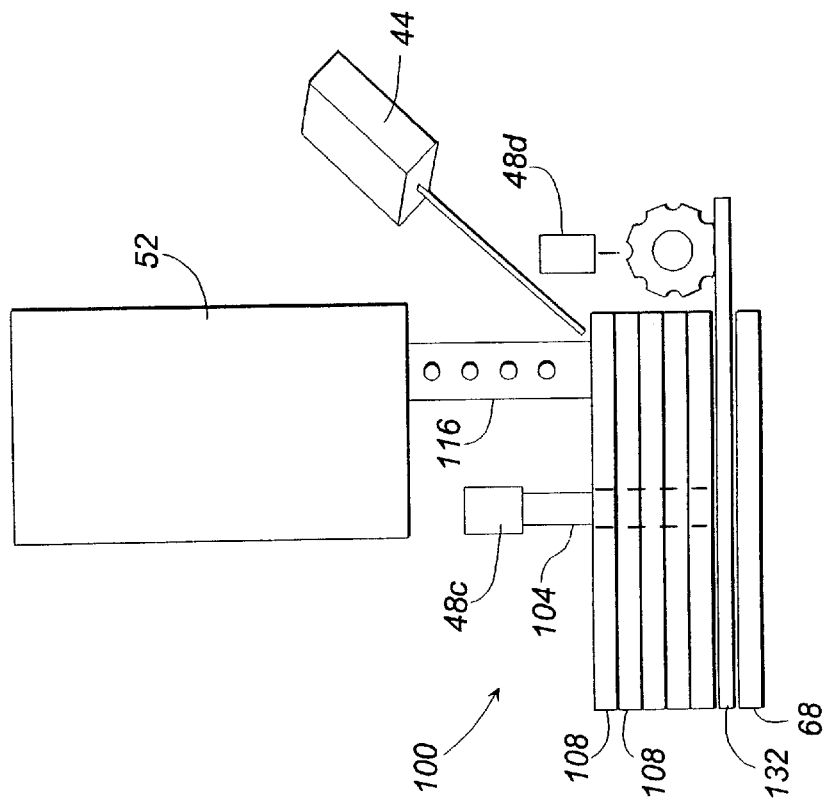
FIG. 7A is an elevation view of the centrifugal pill loader as it is used in the packaging subsystem.

It is at station E that a medication disc 68 is filled with medication from electronic medication counter 52. This is accomplished via centrifugal pill loader 100, which is shown in more detail in FIG. 7A. As best seen in FIG. 7C, centrifugal pill loader 100 is comprised of an elongated alignment adapter 104 on which medication disc templates 108 (see FIG. 7B) can be stacked via an alignment slot 112 in the center of the discs, substantially aligning openings 136. The number of disc templates 108 to be stacked is dependent on the positional relationship of the pill chute 116 coming from electronic medication counter 52. When the desired number of disc templates 108 are loaded, disc template retainer 120 is used to secure the stack to alignment adapter 104 via a retainer ring (not shown). Every time a new medication is loaded into electronic medication counter 52, the disc templates 108 should be discarded and new disc templates 108 loaded onto centrifugal pill loader 100. This will prevent cross contamination of medication resulting from residue left on disc templates 108 from a previous dispensation. The assembled centrifugal pill loader 100 is attached to a drive shaft extending from motor 48c by connecting the drive shaft with alignment adapter 104 via receptacle 124 and then securing the connection with set screw 128. Centrifugal pill loader is suspended over conveyor belt 76b with a trap door 132, which is operated through motor 48d under the control of software program 25 via computer 20 and PLC 46, separating the stacked medication disc templates 108 from a medication disc 68.

With trap door 132 in a closed position, which is defined as being positioned substantially underneath stacked medication disc templates 108, the pills can be dispensed into centrifugal pill loader 100. This is accomplished in step 346 by software program 25 signaling electronic medication counter 52 to count and eject a programmed number of pills into chute 116. As a pill exits chute 116 and is received into one of the openings 136 in stacked medication disc templates 108, reflective scanner 44 detects the pill and signals computer 20 where software program 25, in response to the signal from reflective scanner 44, directs motor 48c through computer 20 and PLC 46 to rotate centrifugal pill loader 100 to position an adjacent opening 136 in alignment with chute 116 for receiving the next pill. This process, which is identified as step 348, continues until the predetermined number of pills are deposited into openings 136 in stacked medication disc templates 108. This determination is represented by decision diamond 350.

After centrifugal pill loader 100 is filled with the programmed number of pills, software program 25 through computer 20 and PLC 46 triggers motor 48d to open trap door 132 to allow the pills to fall into individual compartments in medication disc 68 that correspond to openings 136 in stacked medication disc templates 108 in step 352.

Now that medication disc 68 is filled with pills, medication disc 68 is advanced to station F in step 354. Software program 25 then retrieves a medication label record from data structure 320 in step 356. Next, under the control of software program 25 and computer 20, a translucent cover label is applied by labeling machine 56b in step 358 thereby forming a sealed package. This label contains the required warnings and instructions for use of the medication, and, because it is part of a translucent cover, does not prevent visual inspection of the contents of the package.

Finally, the fully labeled and packaged medication discs 68 are advanced off the end of conveyor belt 76b into hopper 140 in step 360 where they can be manually carried to the sorting station.

Sorting Subsystem

Figure 8A:
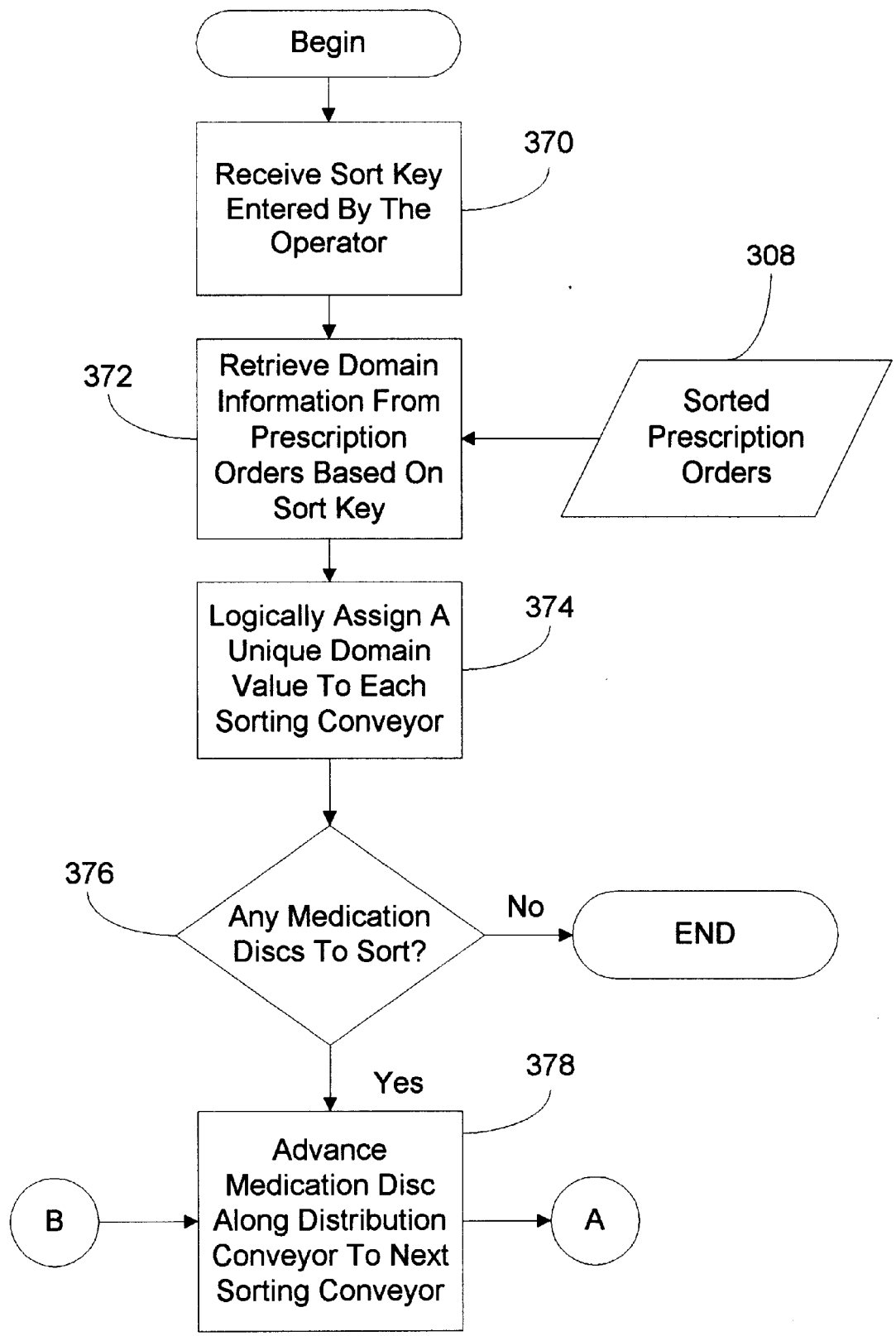
FIG. 8 is a flow chart representing programming tasks and data associated with sorting packaged medication containers.
Figure 8B:
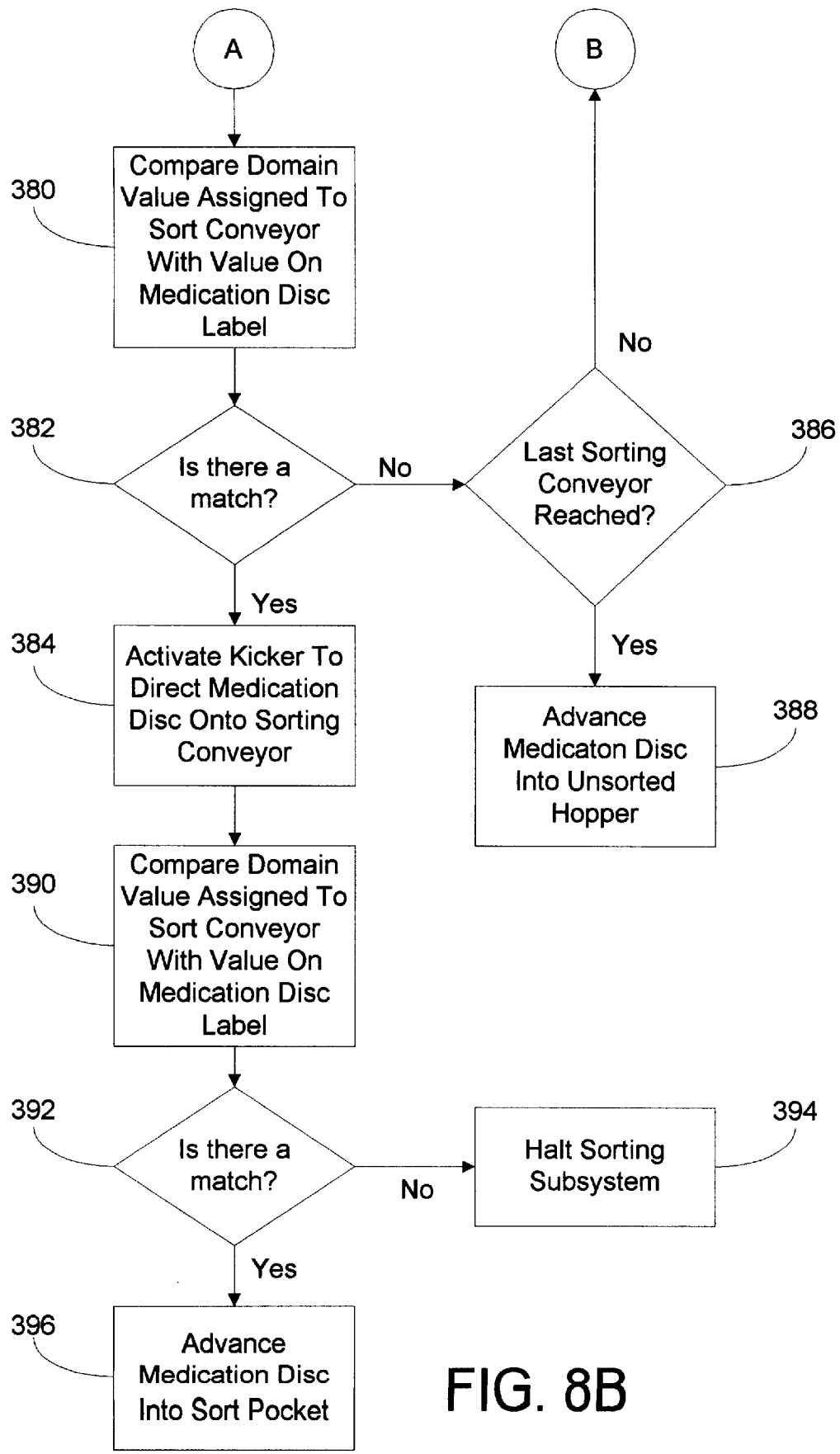

FIG. 8 is a flow chart representing programming tasks and data associated with sorting subsystem 144. This figure will be the subject of frequent reference throughout the discussion of sorting subsystem 64.

Once the prescriptions are labeled and packaged, it is usually necessary to sort medication discs 68 according to various criteria. For example, the batch of medication discs 68 that were packaged could have been based on a single medication type. In that case, the packages will need to be sorted by pharmacy and patient. On the other hand, the batch could have been comprised of prescriptions from a single pharmacy. In that case, the packages will need to be sorted by patient or medication type depending on the pharmacy's preference.

Figure 9:
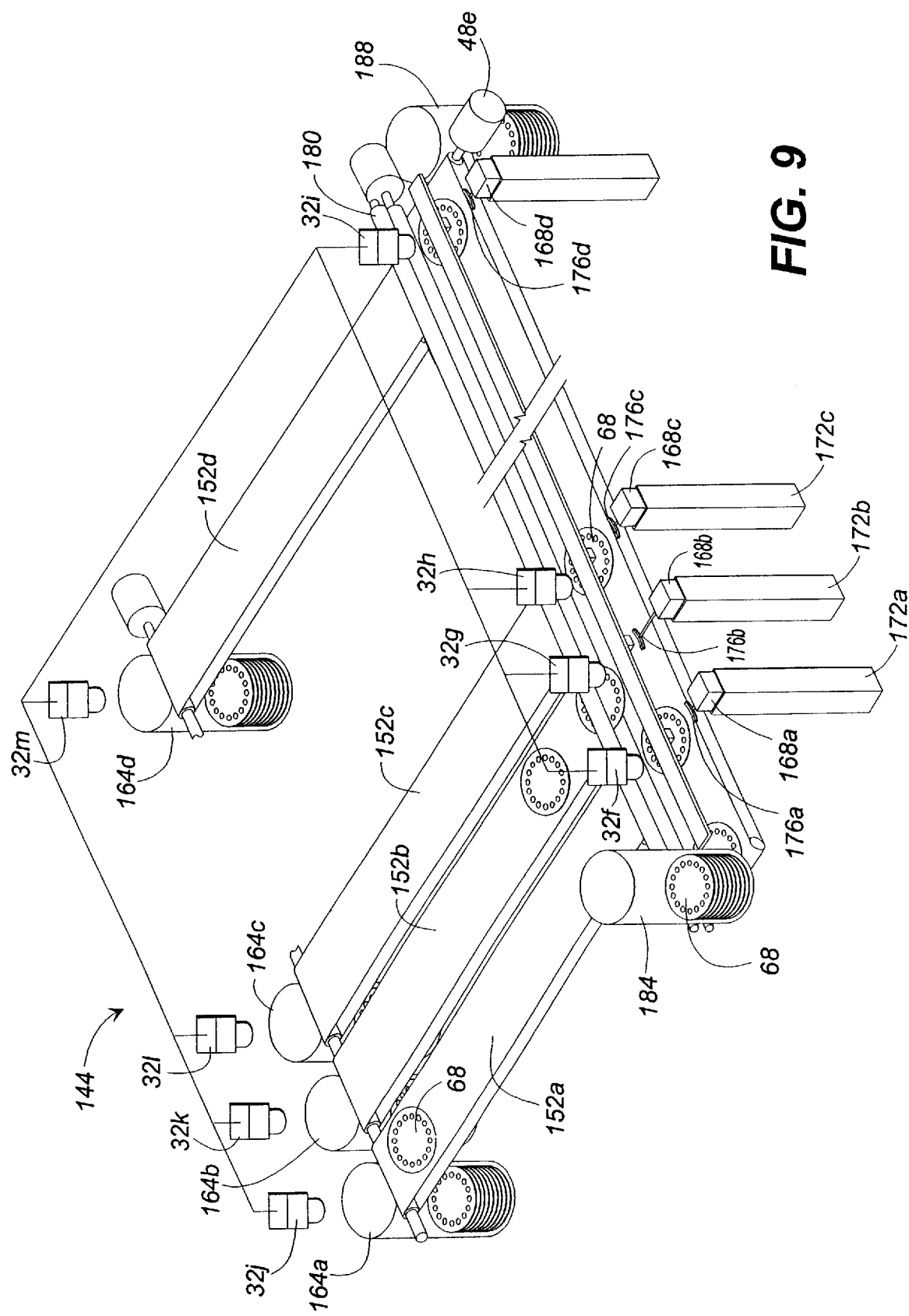
FIG. 9 is a perspective view of the sorting subsystem according to the instant invention.

FIG. 9 illustrates the architecture of the packaged medication disc sorting subsystem 144 according to the present invention. The sorting system includes a distribution conveyor belt 148 and a plurality of sorting conveyor belts 152a,b,c,d positioned transverse to distribution conveyor belt 148. The number of sorting conveyor belts used in practice is a function of the number of sort categories desired. Bar code scanners 32f,g,h,i are mounted above distribution conveyor belt 148 corresponding to each sorting conveyor belt 152a,b,c,d. Optionally, a second set of bar code scanners 32j,k,l,m are mounted above sort pockets 164a,b,c,d. Solenoids 168a,b,c,d are mounted on towers 172a,b,c,d and are controlled through PLC 46. Each solenoid controls a kicker 176a,b,c,d, which is designed to engage medication discs 68 on distribution conveyor belt 148. Feed rollers 180 are interposed between distribution conveyor belt 148 and sorting conveyor belts 152a,b,c,d to facilitate transfer of medication discs 68 from distribution conveyor belt 148 to one of sorting conveyor belts 152a,b,c,d.

With primary reference to FIGS. 8 and 9, the sorting process will now be described. The sorting process begins with step 370 in which the operator enters a sort key (e.g., pharmacy name, patient name, medication identification) into computer 20 through control terminal 28. Based on the sort key entered by the operator, software program 25 will retrieve the domain information (i.e., the range of possible values for the sort key) in step 372 from the sorted prescription orders stored in data structure 308. Each domain value will then be logically assigned to a unique sorting conveyor belt 152a,b,c,d by software program 25 in step 374. Sorting subsystem 144 will begin operation when the packaged medication discs 68 are provided for sorting as represented by decision diamond 376.

Hopper 140 (see FIG. 5), which is filled with fully labeled and packaged medication discs 68, is carried from the packaging and labeling station to sorting subsystem 144 where it is inverted, as illustrated by hopper 184, to gravity feed medication discs 68 to distribution conveyor belt 148 as described hereinbefore with respect to packaging and labeling system 64. Alternatively, packaging subsystem 64 and sorting subsystem 144 could be located in proximity to each other such that a specially designed hopper 140 serves as a conduit transferring medications discs from packaging subsystem 64 to sorting system 144. In step 378, software program 25 will advance the medication discs incrementally through the series of sort conveyors 152a,b,c,d via computer 20, PLC 46 and motor 48e. As the discs are transported along distribution conveyor belt 148, bar code scanners 32f,g,h,i read the desired sort criterion and transmit this information to computer 20 via serial reader 36 and bar code reader 40 where it is processed by software program 25 in step 308. For example, when a medication disc 68 is positioned in front of a given sorting conveyor 152a,b,c,d, software program 25 compares the information read at the bar code scanner with the predetermined assignment for the sorting conveyor to check for a match as represented by decision diamond 382. When software program 25 detects a match between the information read from a medication disc 68 and the sort criteria assigned to the sort conveyor, the software program, through computer 20 and PLC 46, activates the corresponding solenoid 168a,b,c,d in step 384. Activation of the solenoid will in turn trigger its corresponding kicker 176a,b,c,d to nudge medication disc 68 into feed rollers 180 where the disc is then transported along the sorting conveyor into the sort pocket. If no match is detected, software program 25 advances the disc to the next sort conveyor, where, if the last sorting conveyor 152d has not been reached, the process repeats as represented by the "no" branch of decision diamond 386. Clearly, the aforementioned process will be applied to several medication discs in parallel as multiple medication discs assume positions on distribution conveyor 148. If a medication disc 68 traverses all sorting conveyors 152a,b,c,d without being selected, it is advanced off the end of distribution conveyor into unsorted hopper 188 in step 388 where the disc can be manually examined and sorted or returned to hopper 184 to be re-sorted by sorting subsystem 144. Bar code scanners 32j,k,l,m positioned over sort pockets 164a,b,c,d can be used as a verification mechanism to ensure that the medication discs are sorted correctly as indicated in step 390. For example, if the information transmitted from a bar code scanner 32j,k,l,m is inconsistent with the bar code scanner 32f,g,h,i assigned to the same sorting conveyor as indicated by decision diamond 392, software program 25 can halt sorting system 144 in step 394 and notify the operator of the error via terminal 28 or printer 60. Otherwise, the medication discs are advanced into the sort pockets in step 396.

Reclamation Subsystem

Figure 10A:
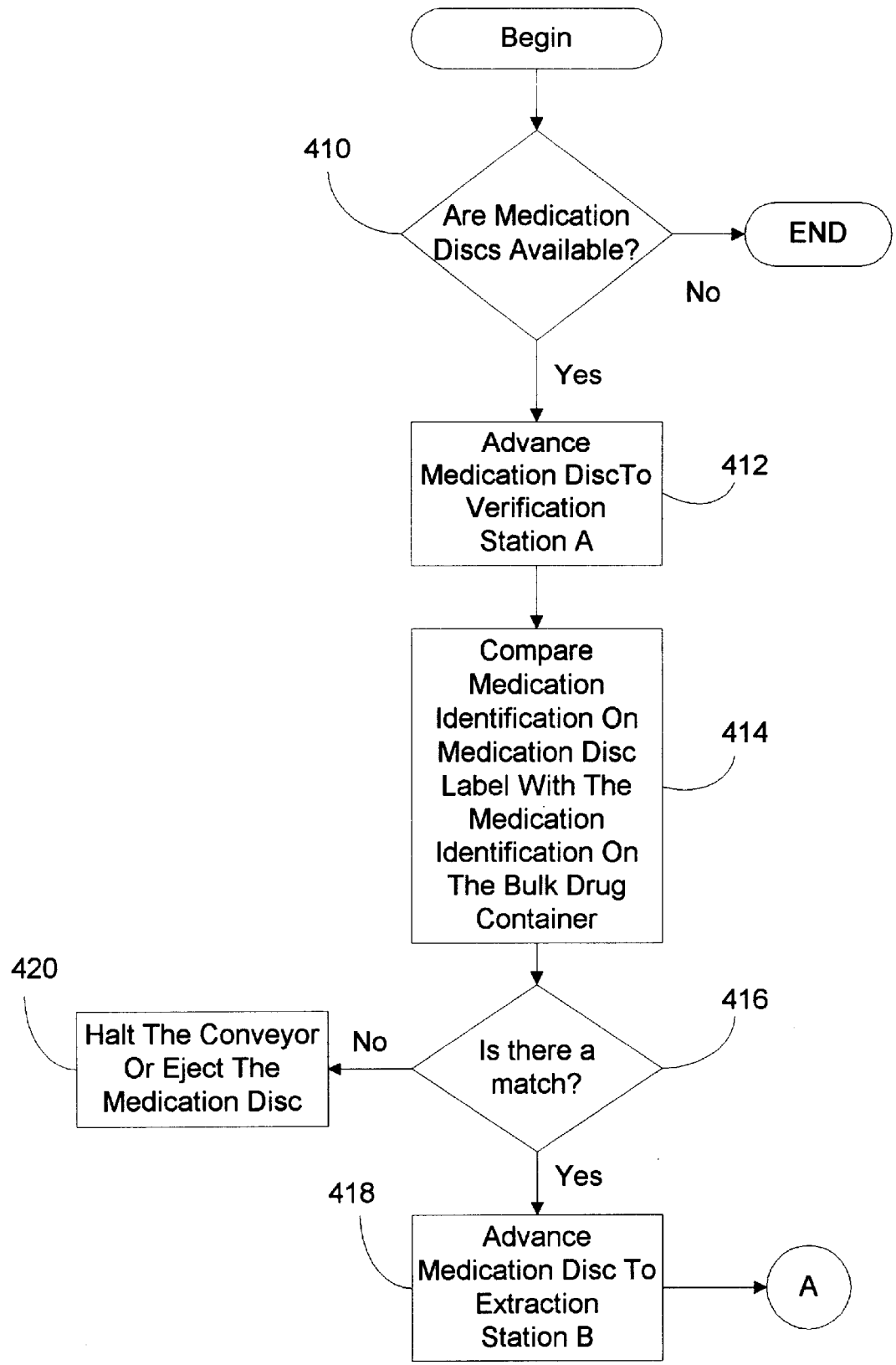
FIG. 10 is a flow chart representing programming tasks and data associated with the reclamation subsystem according to the instant invention.
Figure 10B:
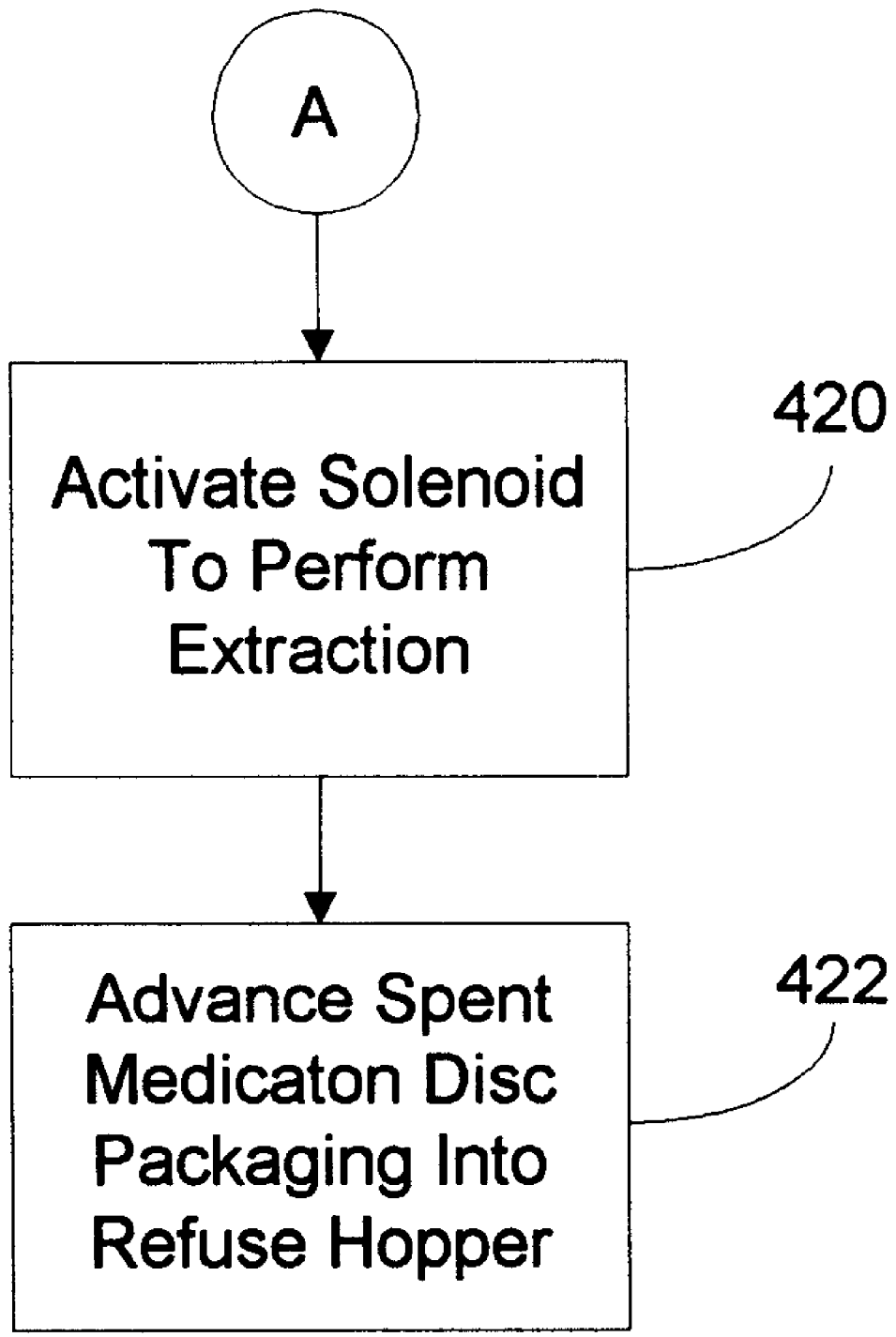

FIG. 10 is a flow chart representing programming tasks and data associated with reclamation subsystem 192. This figure will be the subject of frequent reference throughout the discussion of reclamation subsystem 192.

Figure 11:
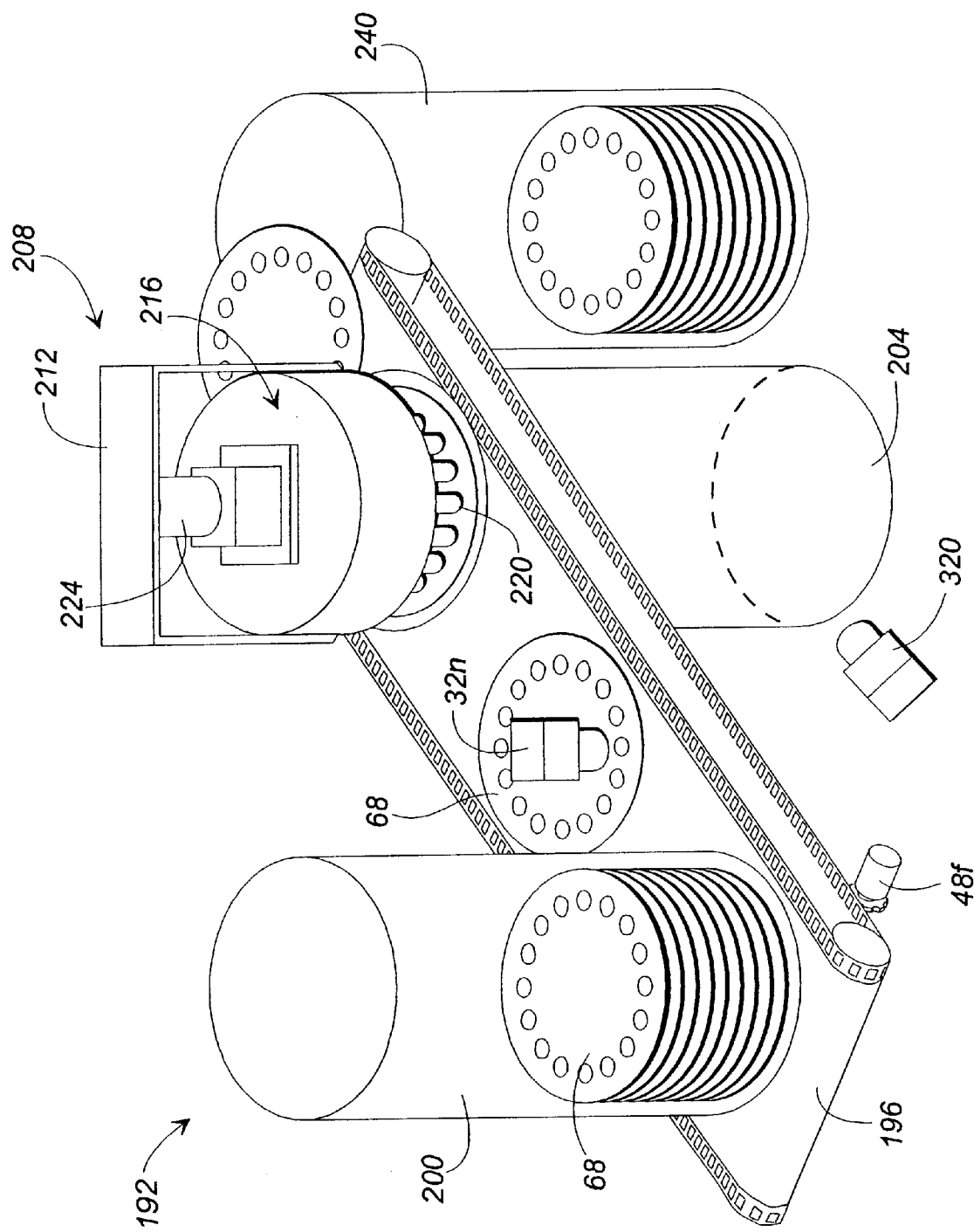
FIG. 11 is a perspective view of the reclamation subsystem according to the instant invention.

As discussed earlier, skyrocketing health care costs make it desirable to recover unused medication instead of destroying it. Unfortunately, no mechanism has been available heretofore for safely reclaiming unused medication. Referring now to FIG. 11, a reclamation subsystem 192 for recovering unused medication from packaged medication discs 68 is shown. Unused medication discs 68 can be sorted by medication type in sorting subsystem 144 and the medication recovered via reclamation subsystem 192 for recycling through packaging subsystem 64.

Again, as discussed hereinbefore with respect to sorting subsystem 144 and packaging subsystem 64, conveyor belt 196 is controlled by software program 25 through computer 20, PLC 46 and motor 48f. Also, medication discs 68 are gravity fed from hopper 200 to conveyor belt 196 to satisfy decision diamond 410 as discussed earlier. Similar to conveyor belts 76a and 76b, conveyor belt 196 contains depressions that are shaped to the contours of a medication disc. However, the depressions in conveyor belt 196 further include apertures corresponding to the arrangement of the medication in medication discs 68.

There are essentially two operating stations in reclamation subsystem 192: verification station A and extraction station B. Bar code scanner 32n is positioned over station A so that when a medication disc 68 reaches station A in step 412, the medication identification information is read from the label and transmitted to computer 20 via serial reader 36 and bar code reader 40. A second bar code scanner is positioned adjacent bulk medication container 204 where the bulk medication identification information is transmitted to computer 20 in the same manner. Software program 25 can then, in step 414, compare the medication type contained in the medication disc with the medication type contained in bulk storage container 204. If the two medication types match at decision diamond 416, the medication disc is advanced to extraction station B in step 418. However, if the medication types do not match, software program 25 will shut down conveyor 196 and assert an error on terminal 28 or printer 60 in step 420. Alternatively, a tower housing a solenoid and a kicker (see, for example, tower 172a, solenoid 168a and kicker 176a in FIG. 9) that is controllable through computer 20 and PLC 46 could be mounted adjacent station A to eject errant discs from conveyor 196 into a hopper in the same manner discs are guided onto sorting conveyors in sorting system 44.

Extractor 208, located at extraction station B, is comprised of a housing 212 that supports extraction disc 216. Extraction disc 216 includes a plurality of extraction posts 220 arranged in a pattern conforming to the arrangement of the medication in medication discs 68. A solenoid 224, which is controlled by software program 25 through computer 20 and PLC 46, is used to engage and disengage extraction disc 216 from conveyor belt 196. Specifically, when a medication disc is positioned underneath extraction disc 216, software program 25 in step 420 signals solenoid 224 to plunge extraction disc 216 down into conveyor belt 196 such that extraction posts 220 penetrate through the medication disc thereby forcing the medication into bulk container 204.

Figure 12:
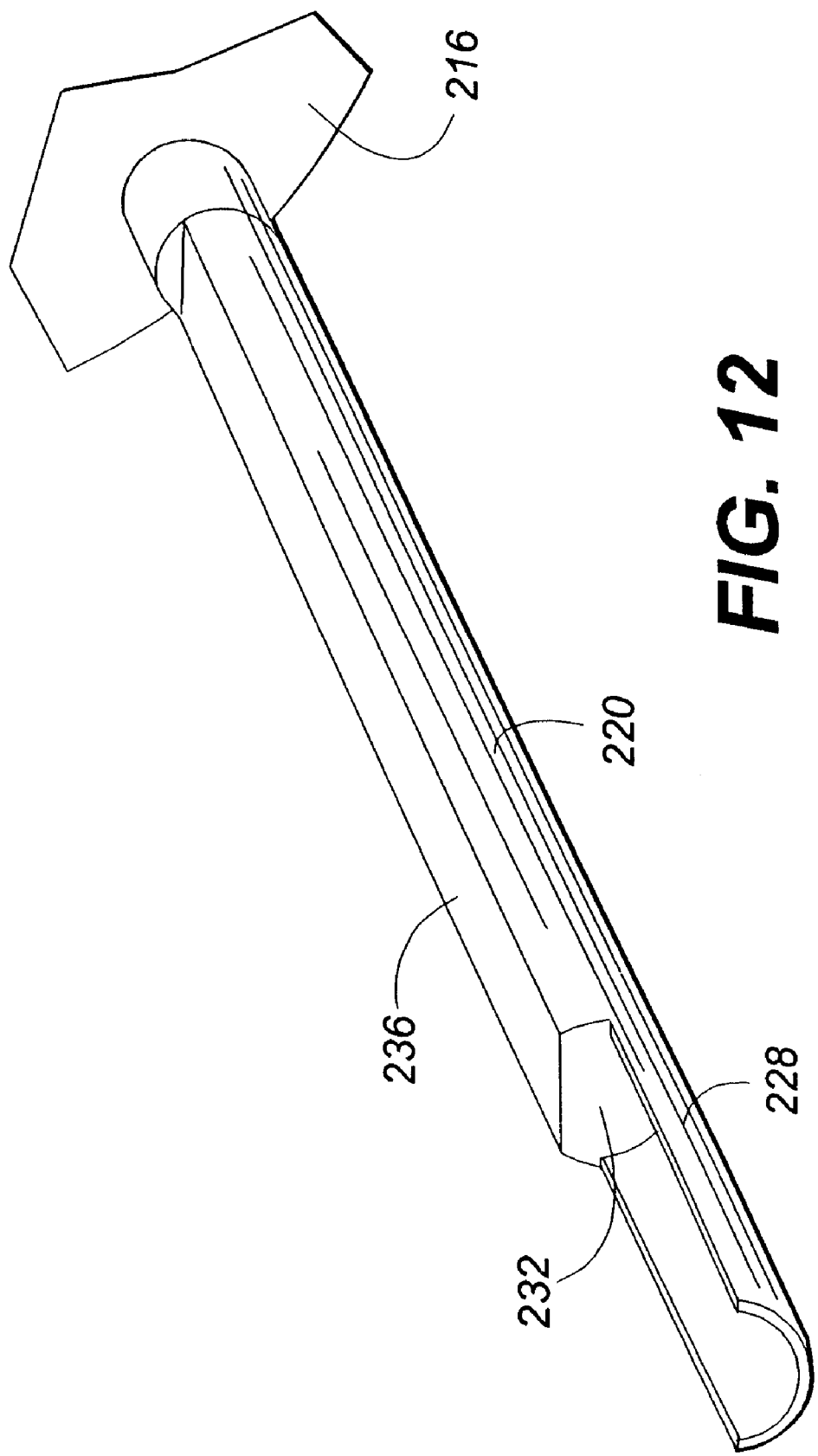
FIG. 12 is a perspective view of the extraction posts.

As shown in FIG. 12, extraction posts 220 are uniquely designed to extract the medication from medication discs 68 without contaminating bulk medication container 204 with packaging material. Specifically, as cutting blade 228 of post 220 pierces the packaging of a medication disc, a substantially flat end portion 232 of post 220 urges the medication out of the packaging so as to ensure the medication is extracted. The cutting blade 228 does not completely severe a portion of the packaging from the disc because flat cutaway surface 236 allows a small portion of the packaging to remain attached. Thus, no packaging material is forced into bulk medication container 204. Extraction posts 220 were originally disclosed in U.S. Pat. No. 5,564,593 to East, which is incorporated herein by reference.

After the medication is extracted at station B, the spent packaging is advanced off the end of conveyor 196 into refuse hopper 240 in step 422.

The principles of the invention have been illustrated herein as they are applied to a system and method for processing prescription medications. From the foregoing, it can readily be seen that the prescription processing system as described herein provides an automated system for filling random prescription orders by grouping these random orders into batches where they can be filled in an economic manner. Moreover, the prescription processing system provides a reclamation system whereby unused medication can be safely recovered and repackaged thereby eliminating the wasteful practice of discarding valuable and still useful medicine.

In concluding the detailed description, it should be noted that it will be obvious to those skilled in the art that many variations and modifications can be made to the preferred embodiment without substantially departing from the principles of the present invention. All such variations and modifications are intended to be included herein within the scope of the present invention, as set forth in the following claims. Further, in the claims hereafter, the corresponding structures, materials, acts, and equivalents of all means or step plus function elements are intended to include any structure, material, or acts for performing the functions with other claimed elements as specifically claimed.

I claim:

1. A batch-type prescription packaging apparatus for packaging medication prescriptions in individual packages, said apparatus comprising:

a control system that controls said apparatus;

a first labeling machine that applies a label to each package which includes medication identification information;

a first scanner that reads the information contained on the package label and forwards the information to said control system;

a sole medication counter adapted to receive a bulk medication cassette filled with a particular medication in pill form, the medication cassette having a label which includes medication identification information that indicates the medication contained in the medication cassette, said medication counter capable of dispensing a predetermined number of pills from the medication cassette and into the package;

a second scanner that reads the medication identification information included in the medication cassette label prior to filling of the package to ensure the information matches the medication identification information included on the package label; and a second labeling machine that applies a cover label to the package to seal the package after the package has been filled with the predetermined number of pills by said sole medication counter;

wherein said apparatus does not include additional medication counters beyond said sole medication counter such that all of the medications packaged by said apparatus are counted by said sole medication counter.

2. The apparatus of claim 1, wherein said sole medication counter is an electronic medication counter.

3. The apparatus of claim 1, wherein said medication identification information included on the package label is bar code information and wherein said first scanner is a bar code scanner.

4. The apparatus of claim 1, wherein said medication identification information included on the medication cassette is bar code information and wherein said second scanner is a bar code scanner.

5. The apparatus of claim 1, further comprising a third scanner that counts the number of pills dispensed by said sole medication counter to ensure the correct number of pills have been dispensed.

6. The apparatus of claim 1, farther comprising at least one conveyor which conveys the package from the first labeling machine, to the sole medication counter, and then to the second labeling machine.

7. The apparatus of claim 6, wherein said at least one conveyor includes a conveyor belt having a plurality of depressions formed therein, each depression being adapted to receive a package.

8. The apparatus of claim 1, further comprising a centrifugal medication loader that comprises a template having an alignment slot and a plurality of openings for receiving medication, an alignment adapter that receives said template, securing means for fastening said template to said alignment adapter, and rotation means connected to said alignment adapter.

9. The apparatus of claim 8, wherein said centrifugal medication loader further comprises a trap door and means for operating said trap door.

10. A batch-type prescription packaging apparatus for packaging medication prescriptions in individual packages, said apparatus comprising:

a control system that controls said apparatus;

a first labeling machine that applies a label to each package which includes medication identification information;

a first scanner that reads the information contained on the package label and forwards the information to said control system;

a medication counter adapted to receive a bulk medication cassette filled with a particular medication in pill form, the medication cassette having a label which includes medication identification information that indicates the medication contained in the medication cassette, said medication counter capable of dispensing a predetermined number of pills from the medication cassette and into the package;

a second scanner that reads the medication identification information included in the medication cassette label prior to filling of the package to ensure the information matches the medication identification information included on the package label; and a second labeling machine that applies a cover label to the package to seal the package after the package has been filled with the predetermined number of pills by said medication counter;

wherein said medication counter is used to count a variety of different medications in batch form.

* * * * *